US006351661B1

(12) United States Patent
Cosman

(10) Patent No.: US 6,351,661 B1
(45) Date of Patent: *Feb. 26, 2002

(54) OPTICALLY COUPLED FRAMELESS STEREOTACTIC SPACE PROBE

(75) Inventor: Eric R. Cosman, Belmont, MA (US)

(73) Assignee: Sherwood Services AG, Schaffhausen (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/212,326

(22) Filed: Dec. 14, 1998

Related U.S. Application Data

(63) Continuation of application No. 08/482,213, filed on Jun. 7, 1995, now Pat. No. 5,848,967, which is a division of application No. 08/441,788, filed on May 16, 1995, now Pat. No. 5,662,111, which is a continuation of application No. 08/299,987, filed on Sep. 1, 1994, now abandoned, which is a continuation of application No. 08/047,879, filed on Apr. 15, 1993, now abandoned, which is a continuation of application No. 07/941,863, filed on Sep. 8, 1992, now abandoned, which is a continuation of application No. 07/647,463, filed on Jan. 28, 1991, now abandoned.

(51) Int. Cl.[7] ................................................. A61B 5/00
(52) U.S. Cl. ...................... 600/426; 600/411; 600/414; 600/417; 600/427; 600/429; 606/130
(58) Field of Search ................. 606/130; 600/411, 600/414, 417, 426, 427, 429

(56) References Cited

U.S. PATENT DOCUMENTS 3,821,469 A    6/1974   Whetsone et al.
3,983,474 A    9/1976   Kuipers
4,058,114 A   11/1977   Soldner (List continued on next page.)

FOREIGN PATENT DOCUMENTS

| EP | 0 018 166 | 10/1980 |
| EP | 0 062 941 | 10/1982 |
| EP | 0 326 768 |  8/1989 |

(List continued on next page.)

OTHER PUBLICATIONS

Kosugi, Yukio et al., "An Articulated Neurosurgical Navigation System Using MRI and CT Images", IEEE *Transactions on Biomedical Engineering*, vol. 35, No. 2, pp. 147–152, Feb. 1988.

Adams, Ludwig et al., "Computer–Assisted Surgery", IEEE *Computer Graphics & Applications*, pp. 43–51, May 1990.

(List continued on next page.)

*Primary Examiner*—Ruth S. Smith

(57) ABSTRACT

A system for quantitative computer graphic determination of positions on a patient's anatomy and positions on associated equipment located near the patient's anatomy in relation to anatomical data, as from CT or MR scanning. A first camera produces a quantitative electronic readout of its field-of-view which provides a determination of relative spacial coordinates of uniquely identifiable points in its field-of-view. A second camera produces a quantitative electronic readout of its field-of-view which provides a determination of relative spacial coordinates of uniquely identifiable points in its field-of-view. The two cameras are located with respect to the patient's anatomy and the associated equipment so that the fields-of-view of the cameras include both the patient's anatomy and the equipment, but are taken from different directions. A body marker is positioned with respect to the patient's anatomy at a known position relative to said patient anatomy. The body marker has known coordinates in a stereotactic coordinate system that is established relative to the patient's anatomy so that the coordinates of all identifiable points in the fields of view of the two cameras can be determined relative to the stereotactic coordinate system and related to imaging data.

24 Claims, 4 Drawing Sheets

U.S. PATENT DOCUMENTS

| | | |
|---|---|---|
| 4,068,156 A | 1/1978 | Johnson et al. |
| 4,068,556 A | 1/1978 | Foley |
| 4,182,312 A | 1/1980 | Mushabac |
| 4,262,306 A * | 4/1981 | Renner ................... 600/130 |
| 4,341,220 A | 7/1982 | Perry |
| 4,358,856 A | 11/1982 | Stivender et al. |
| 4,407,298 A | 10/1983 | Lentz et al. |
| 4,457,311 A | 7/1984 | Sorenson et al. |
| 4,465,069 A | 8/1984 | Barbier et al. |
| 4,473,074 A | 9/1984 | Vassiliadis |
| 4,506,676 A | 3/1985 | Duska |
| 4,571,834 A | 2/1986 | Fraser et al. |
| 4,583,538 A | 4/1986 | Onik et al. |
| 4,592,352 A | 6/1986 | Patil |
| 4,602,622 A | 7/1986 | Bär et al. |
| 4,608,977 A | 9/1986 | Brown |
| 4,638,798 A | 1/1987 | Shelden et al. |
| 4,645,343 A | 2/1987 | Stockdale et al. |
| 4,651,732 A | 3/1987 | Frederick |
| 4,659,971 A | 4/1987 | Suzuki et al. |
| 4,660,970 A | 4/1987 | Ferrano |
| 4,674,057 A | 6/1987 | Caughman et al. |
| 4,686,997 A | 8/1987 | Oloff et al. |
| 4,698,777 A | 10/1987 | Toyoda et al. |
| 4,701,049 A | 10/1987 | Beckmann et al. |
| 4,701,407 A | 10/1987 | Appel |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,722,056 A | 1/1988 | Roberts et al. |
| 4,723,544 A | 2/1988 | Moore et al. |
| 4,733,661 A | 3/1988 | Palestrant |
| 4,733,969 A | 3/1988 | Case et al. |
| 4,737,032 A | 4/1988 | Addleman et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,128 A | 6/1988 | Barlett et al. |
| 4,753,528 A | 6/1988 | Hines et al. |
| 4,761,072 A | 8/1988 | Pryor |
| 4,762,016 A | 8/1988 | Stoughton et al. |
| 4,764,016 A | 8/1988 | Johanasson |
| 4,776,749 A | 10/1988 | Wanzenberg et al. |
| 4,779,212 A | 10/1988 | Levy |
| 4,791,934 A | 12/1988 | Brunnett |
| 4,794,262 A | 12/1988 | Sato et al. |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,822,163 A | 4/1989 | Schmidt |
| 4,825,091 A | 4/1989 | Breyer et al. |
| 4,829,373 A | 5/1989 | Leberl et al. |
| 4,835,710 A | 5/1989 | Schnelle et al. |
| 4,836,778 A | 6/1989 | Baumrind et al. |
| 4,841,967 A | 6/1989 | Chang et al. |
| 4,875,478 A | 10/1989 | Chen |
| 4,896,673 A * | 1/1990 | Rose et al. ................. 600/439 |
| 4,931,056 A | 6/1990 | Ghajar et al. |
| 4,933,843 A | 6/1990 | Scheller et al. |
| 4,943,296 A | 7/1990 | Funakubo et al. |
| 4,945,914 A | 8/1990 | Allen |
| 4,954,043 A | 9/1990 | Yoshida et al. |
| 4,955,891 A | 9/1990 | Carol |
| 4,961,422 A | 10/1990 | Marchosky et al. |
| 4,991,579 A | 2/1991 | Allen |
| 5,016,639 A | 5/1991 | Allen |
| 5,017,139 A | 5/1991 | Mushabac |
| 5,027,818 A | 7/1991 | Bova et al. |
| 5,047,036 A | 9/1991 | Koutrouvelis |
| 5,050,608 A | 9/1991 | Watanabe et al. |
| 5,078,140 A | 1/1992 | Kwoh |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,099,836 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,186,174 A | 2/1993 | Schlöndorff et al. |
| 5,193,106 A | 3/1993 | DeSena |
| 5,197,476 A | 3/1993 | Nowacki et al. |
| 5,207,223 A | 5/1993 | Adler |
| 5,211,164 A | 5/1993 | Allen |
| 5,224,049 A | 6/1993 | Mushabac |
| 5,230,338 A | 7/1993 | Allen et al. |
| 5,251,127 A | 10/1993 | Raab |
| 5,305,203 A | 4/1994 | Raab |
| 5,383,454 A | 1/1995 | Bucholz |
| 5,389,101 A | 2/1995 | Heilbrun et al. |
| 5,617,857 A | 4/1997 | Chader |
| 5,622,170 A | 4/1997 | Schulz |
| 5,662,111 A * | 9/1997 | Cosman ................... 600/429 |
| 5,848,967 A * | 12/1998 | Cosman ................... 600/426 |
| 6,006,126 A * | 12/1999 | Cosman ................... 600/426 |

FOREIGN PATENT DOCUMENTS

| | | |
|---|---|---|
| EP | 0 359 773 | 3/1990 |
| FR | 2417-970 | 10/1979 |
| GB | 2 094 590 | 9/1982 |
| WO | WO 90/05494 | 5/1990 |
| WO | WO 91/07726 | 5/1991 |

OTHER PUBLICATIONS

Wolfe, William L., et al., "Image Trackers", *The Infrared Handbook*, Environmental Research Institute of Michigan for the Office of Naval Research, 1978, pp. 22–63 –22–67 and 22–74 –22–77 (Chapter from a Book).

Castelman, Kenneth R., "Stereometric Ranging", *Digital Image Processing*, Prentice–Hall, Inc., Englewood Cliffs, New Jersey 1979, pp. 364–369 (Chapter from a Book).

Foley, James D., et al., "Geometrical Transformations", *Fundamentals of Interactive Computer Graphics*, Second Edition, Addison–Wesley Publishing Company, 1984, Chapter 7, pp. 245–266 (Chapter from the Book).

Newman and Sproull, "Moving Parts Of An Image", *Principles of Interactive Computer Graphics*, McGraw–Hill Book Company, 1979, Section 17.3, p. 254 (Section from a Book).

* cited by examiner

OPTICALLY COUPLED FRAMELESS STEREOTACTIC SPACE PROBE

This is a continuation of application Ser. No. 08/482,213, filed Jun. 7, 1995, now U.S. Pat. No. 5,848,967, which is a divisional application of application Ser. No. 08/441,788, filed May 16, 1995, now U.S. Pat. No. 5,662,111, which is a continuation of application Ser. No. 08/299,987, filed Sep. 1, 1994, now abandoned, which is a continuation of application Ser. No. 08/047,879, filed Apr. 15, 1993, now abandoned, which is a continuation of application Ser. No. 07/941,863, filed Sep. 8, 1992, now abandoned, which is a continuation of application Ser. No. 07/647,463, filed Jan. 28, 1991, now abandoned.

BACKGROUND TO THE INVENTION

The concept of frameless stereotaxy is now emerging in the field of neurosurgery. What is meant by this is quantitative determination of anatomical positions on, let us say, the head based on data taken from a CT, MRI or other scanning needs. The data from the image scan can be put into a computer and the head represented, according to this graphic information. It is useful for the surgeon to know where he will be operating relative to this data field. He can, thus, plan his operation quantitatively based on the anatomy as visualized form the image data. Until now the use of stereotactic head frames for fixation means is commonplace. For example, see U.S. Pat. No. 4,608,977, issued Sep. 2, 1986, and entitled: System Using Computed Tomography As For Selective Body Treatment, Brown. These employ a head fixation device typically with an index means that can be visualized in scan slices or image data. Thus, the anatomical stereotactic data so determined can be quantified relative to the head frame. Arc systems or probe carriers are typically used to direct a probe quantitatively based on this data relative to the head holder and, thus, to the anatomy. If the surgeon can be freed from the use of the head holder and localizer, and still relate positions in the anatomy to things seen on the scan or image data, then this can spare patient discomfort and could be potentially used for general neurosurgery where only approximate target positioning is needed. For example, a space pointer which could be directed to the anatomy and its position could be quantified relative to the stereotactic image data. This space pointer, analogous to a pencil, might be therefore pointed at a position on the anatomy and the position and the direction of the pointer, subsequently appear, on the computer graphics display of the anatomical data. Such apparatus has been proposed, using an articulated space pointer with a mechanical linkage. In that regard, see an article entitled "An Articulated Neurosurgical Navigation System Using MRI and CT Images," IEEE Transactions on Biomedical Engineering, Volume 35, No. 2, February 1988 (Kosugi et al), incorporated by reference herein. It would be convenient if this space pointer were mechanically decoupled or minimally mechanically coupled. Until now, several attempts have been made to implement a passive or active robotic pointer as described in the referenced article, essentially, which consists of a pencil attached to an articulating arm, the arm having encoded joints which provide digital angular data. Such a robotic space pointer is a mechanically attached device and once calibrated can give the graphic representation of the pointer on a computer screen relative to the stereotactic data of the head.

One objective of the present invention is to provide a camera apparatus (optical) which can visualize a surgical field and digitize the view information from the camera and relate it via computer graphics means to image data which has been taken of the patient's anatomy by image scanning means (tomographic scanner). The relationship of the optical camera view and the image data will then make quantitative the anatomy seen in the camera view and also make quantitative the position of surgical instruments such as probes, microscopes, or space pointers to the anatomy via the registration of the camera view to the image data.

Another objective of the present invention is to make an optically coupled space pointer which accomplishes the same objectives as the robotic arm mechanically coupled space pointer, e.g., give ongoing positional correspondence between a position in a patient's brain and the tomographic image (see Kosugi et al). The optical coupling would free the surgeon from any sterility questions, provide an obstruction-free device, and avoid the encumbrances of a bulky mechanically coupled instrument.

DESCRIPTION OF THE INVENTION

Figure 1:
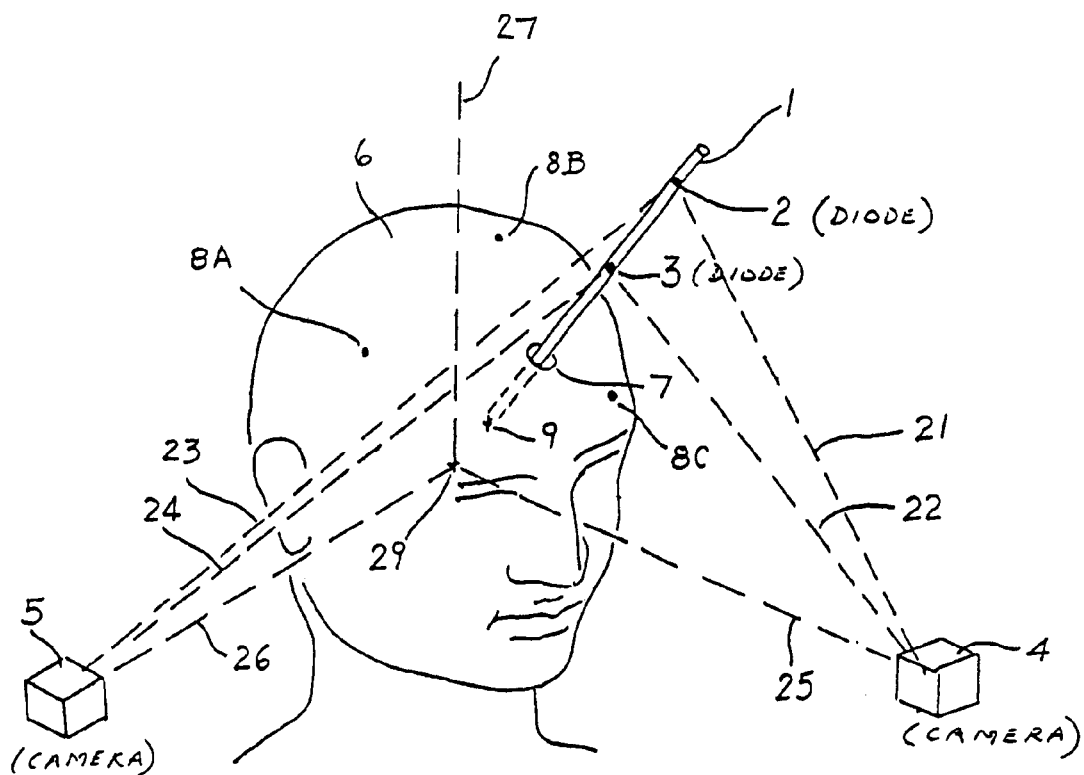
FIG. 1 shows one embodiment of the present invention which involves two video cameras and a space pointer with two light sources on it.

FIG. 1 shows a schematic view of one embodiment of the invention. The setting is neurosurgery and the patient's head 6 is being operated on through a skull hole 7. Probe 1 is being put to the patient's head and it is desired to know the relationship of that probe 1 to the anatomy of the patient's head 6 as visualized from some imaging means such as CT or MR scanners or angiographic X-rays views. This image data representation of the patient's head would previously have been accumulated in a computer, see the referenced U.S. Pat. No. 4,608,977.

Figure 5:
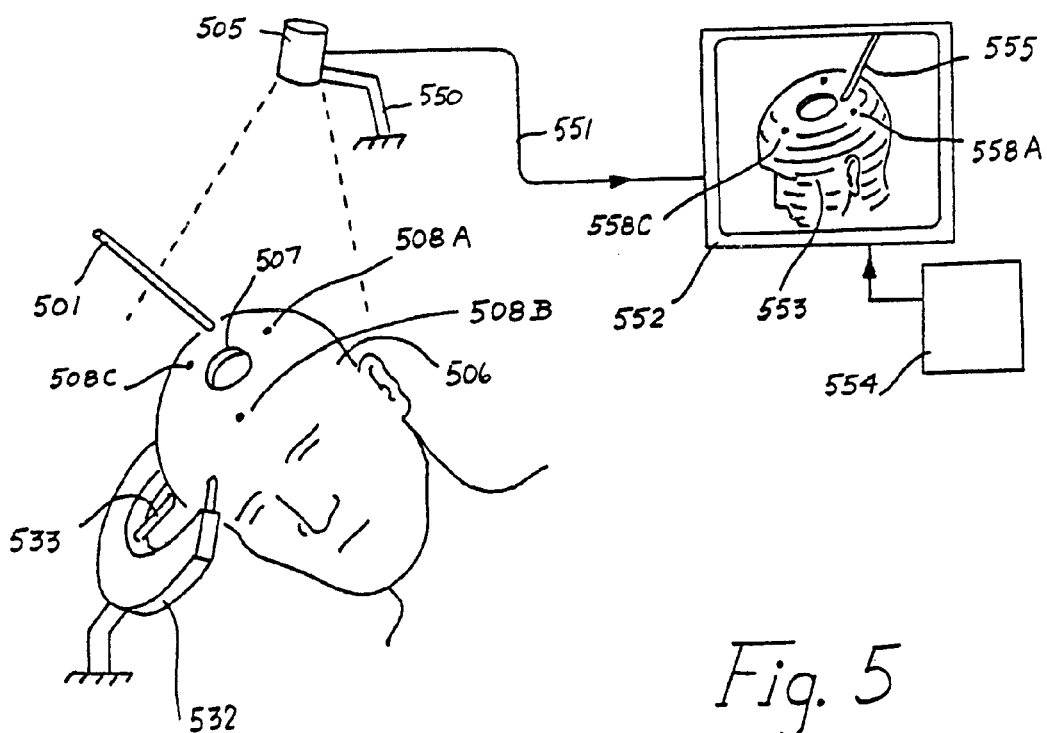
FIG. 5 shows a generalized, signal camera embodiment of the invention where the camera is coupled to a computer graphic means and the view of the camera looking at the patient anatomy is related to image data from image scan means so as to register the camera view and the image data to quantify the camera view field.

The cameras 4 and 5 may, for example take the form of known devices, e.g., CCD Type compact TV Scanners with high resolution that can be easily digitized and video displayed or displayed on computer graphic screens, see FIG. 5. The cameras 4 and 5 may operate as disclosed in a book: Digital Image Processing, Second Edition, Addison-Wesley Publishing Company, Gonzalez and Wintz, 1987, incorporated by reference herein. Specifically, using stereoscopic imaging techniques to map points sensed in a world coordinate system is treated in a section 2.5.5 entitled "Stereo Imaging," beginning on page 52. As explained in the book, the two cameras 4 and 5 are used to find the coordinates (X, Y and Z) of light sources 2 and 3. Detailed treatment of cameras as imaging trackers appears in a book: The Infrared Handbook, incorporated by reference herein and prepared by the Environmental Research Institute of Michigan (1978) for the Office of Naval Research, see pages 22–63 through 22–77. See also, a book: Digital Image Processing, Prentice-Hall, Inc., by Kenneth R. Castleman, published in Englewood Cliffs, N.J., 1979, incorporated by reference herein and specifically a section entitled "Stereometric Ranging," beginning on page 364.

In FIG. 1, the cameras 4 and 5 are looking at the field including the patient's head 6 and the probe 1.

The orientation and quantification of the camera coordinate data taken from the scan images in the video cameras can be registered by index spots 8A, 8B and 8C placed on the patient's head. An alternative to these index spots might be a head ring which is fixed firmly to the patient's skull as is commonly done in surgery and that headring may have index points or lines on it which can be seen in the two views from the cameras 4 and 5. When the index points are in view of the cameras 4 and 5, the appropriate transformations can be made if the coordinates of the physical points 8A, 8B, and 8C are known beforehand to the entire data set (CT or MR) of anatomy in the computer as indicated. Thus, the reference points are used to relate the camera data to the stored anatomical data coordinates. More than three points may also be used for redundancy or better field of view. As indicated, the probe in FIG. 1 has two index light sources 2 and 3, which are also visible within a certain range to the cameras 4 and 5. Thus, the orientation of the light sources 2 and 3 relative to the anatomy is registered by the two cameras 4 and 5 and thus physical orientation of probe 1 relative to the stored CT or MR data on the head 6 is known. Since light sources 2 and 3 may be in a predetermined orientation relative to the tip 9 of the probe 1, the actual physical location of the tip 9 relative to the anatomy may also be computed by the data of the two views of the cameras 4 and 5.

With the locations of the sources 2 and 3 specified, the orientation of the probe 1 may also be determined from these two camera views. Thus, it is possible to display by the data accumulated by the cameras 4 and 5, the orientation and absolute position of the probe 1 relative to the anatomy data, and this display can be made in computer graphics real time as the probe 1 is moved around in a field near the anatomy e.g., the head 6. In particular, the probe 1 position within the entry hole 7 is known, and thus the tip 9 can be graphically visualized on a computer display relative to the stored anatomy inside the patient's head. This is most useful when exploring the interior of a surgical hole when the surgeon wishes to know the advancement of his probe or surgical instruments within that hole. Such an instrument may also be useful in planning the position of a surgical incision. By pointing the probe at the patient's skin and being able to visualize the position on the skin relative to relevant anatomy inside the head, the surgeon can make a judicious choice of entry point.

The light sources 2 and 3 may be LED light sources of very small dimension and they can be powered by an internal battery in the probe 1. The probe may thus be mechanically decoupled from other apparatus and only optically coupled through the cameras 4 and 5. This optical coupling can be done in other ways. For example, there may be external light sources positioned nearby which can be reflected by tiny reflectors that function as the light sources 2 and 3 on the probe. The reflected light can then be detected by cameras 4 and 5 giving the same optical registration of the probe position as though the light sources 2 and 3 were sources of direct light from the probe itself.

Recalibration of the entire optical system is also possible. Cameras 4 and 5 may have principle optical axes, 25 and 26 respectively shown in FIG. 1. The cameras can be aligned to point in a plane and directed towards a common isocenter 29. Thus all rays in the field such as rays 21 and 22 as seen from camera 4 to points 2 and 3 or rays 23 and 24 which also connect points 2 and 3 on the probe to the camera 5 can be calibrated in the field of the cameras so that their exact angles relative to the principle rays indicated by 25 and 26 can be quantitatively determined. Once the quantitative orientation of these rays to the fiducial points 2 and 3 are digitized and determined numerically, then the position and orientation of the probe 1 can be calculated relative to the point 29 which as been recalibrated as explained below. The exact referencing of the coordinate system represented by axes 25 and 26 with their crossover point 29 and orthogonal axis 27 can be determined by further fiducial points on the anatomy itself. Natural anatomical fiducial points can be used such as the tip of the nose, the ears or other bony landmarks. However, specific index points such as 8A, 8B, and 8C can be placed on the patient's scalp, for example, and these used as a reference transformation set to relate the data seen by the cameras to anatomical data determined from the imaging. For example, the exact coordinates of the points 8A, 8B, and 8C may have been determined in space from the scan data previously. By knowing their exact coordinates in space and knowing the position of other anatomy relative to them, by determining the position as seen by the cameras 4 and 5 of these three fiducial points, the rest of the anatomy can also be registered in the cameras field. Thus the exact positioning of these fiducial points onto the graphic display of the anatomical data from the images can be made. Furthermore, the exact positioning of the probe with its fiducial points 2 and 3 can be thus set quantitatively into the field in a similar way. This operation corresponds to a series of 3-dimensional coordinate transformations and is a straight-forward mathematical matter. Specifically, mathematical transformations are well known in the computer graphics prior art as treated in the textbook: Fundamentals of Interactive Computer Graphics, Addison-Wesley Publishing Company, 1982, Foley and Van Dam, incorporated by reference herein, see Chapter 7 entitled "Geometrical Transformations."

Figure 2:
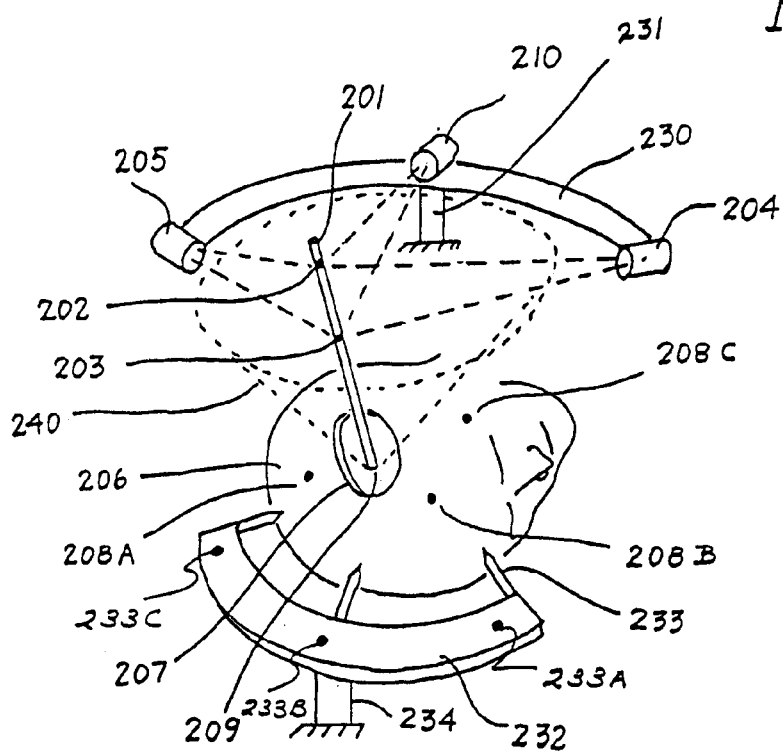
FIG. 2 shows an embodiment of the present invention with the space pointer pointing into a cranial operative site and where more than two video cameras are looking at the space pointer for redundancy.

FIG. 2 illustrates another embodiment to the present invention in which more than two cameras are involved. Cameras 204 and 205, as well as camera 210, are present and may prealigned or not prealigned prior to surgery. They are anchored on a support structure 230 which holds them rigidly in place and that support, in turn, is clamped by means of clamping means 231 to some stable object relative to the patient's head 206 such as the operating room table or the floor itself. Headholder 232 may be a standard headholder as used in most operations with pin fixation points to the skull illustrated by 233, it too can be anchored to the operating table or to the floor by post 234 and, thus, the optical system above it and the head holder are stabilized relative to each other by means of their attachment to either themselves or to the operating table. Again, the index points 202 and 203 (light sources) represent the fiducial points for the cameras 204, 205 and 210 and by digitizing the field of these cameras, one can determine the position and orientation of the probe 201 in space coordinates. In addition, there are the index reference points 208A, B, and C which represent independent fiducial points on the patient's head which can be also observed by the cameras and the cameras can, therefore, check the stability as well as their coordinate reference frame continuously by monitoring these fiducial points on the anatomy itself. There is a typical range of motion of the probe 201 which is practical in such operations and this is illustrated as an example by the dashed-line cone 240. It must be that the cameras can visualize the probe 201 and the fiducial points 202 and 203 everywhere within the working cone 240. This is typically the range in which the surgeon will be introducing instruments into the cranial opening site 207. It is clear that the positions of the cameras 204, 205 and 210 can be prearranged and precalibrated on the bar 230. This may be done so that they are pointing isocentrically to the same point in that their visualization fields are precalibrated and preoriented so that everything within the field has a known calibration. This could also be easily checked by taking the platform 230 off at any given time and putting it on a phantom base or some other jig structure which enables instant calibration of the system. It is also true that the head holder 232 may have fiducial lights on it or fiducial points 233A, 233B and 233C so that it may be referenced relative to the cameras and the entire system becomes an integral digitized calibrated system.

Figure 3:
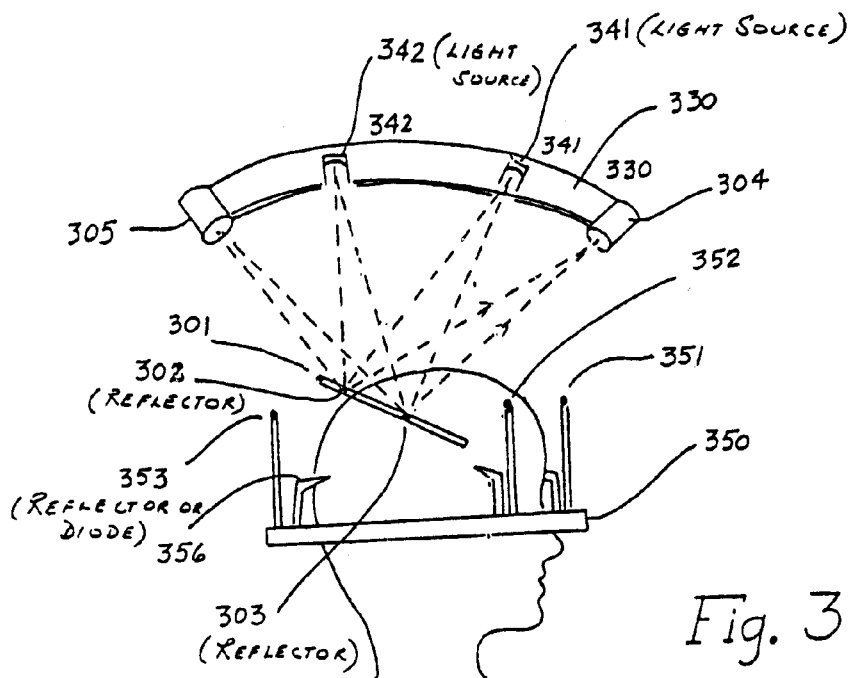
FIG. 3 shows an embodiment of the present invention in which light sources at a distance from the pointer are used to reflect off reflectors on the pointer and the reflected light is detected by video cameras to ascertain the orientation of the space pointer.

FIG. 3 shows another embodiment of the present invention in which external light sources 341 and 342 are present as well as the cameras 304 and 305 for receiving optical signals. Cameras 304 and 305 are arranged and fixed to a bar 330 for positioning. Light sources 342 and 341 are also arranged and attached to the bar 330 so that they aim towards the probe 301 which has reflectors on it, specifically sources 302 and 303 which reflect the light from the light sources 341 and 342. The cameras 304 and 305 detect the reflected light which is illustrated by the dashed-line light beams shown in FIG. 3. In this way the probe 301 does not have to have any energy source or active light sources, but can be merely a reflector of light. It is also true that the probe itself could be one, long reflective linear arrangement or could have other arrangements of the fiducial points instead of the linear arrangement 302, which is coaxial with the probe. Any kind of pattern recognition of this type could be detected by the cameras 304 and 305 and the corresponding digitization of the probe position and orientation could be made.

In this example of FIG. 3 we also show headring 350 which is affixed to the patient's head by a series of head posts 356 anchored securely to the skull. On the headring are fiducial elements 351, 352 and 353 which serve as index points and reference points that can also be detected optically by the cameras 304 and 305. In this way, the ring 350 represents a platform and corresponding coordinate system basis, the position of the coordinate system being referenced by the fiducial points 351, 352 and 353 and monitored in terms of its relative position to the bar 330 and its associated cameras. In this way the entire operative setting could be monitored for any differences in position and position differences can be corrected for if they are determined by the computer graphics associated with the cameras 304 and 305. It is notable that the need for discrete index points such as 302 and 303 on the space pointer is not absolutely necessary. Pattern recognition algorithms in a computer from data from cameras 304 and 305 may simply recognize the shape of the space pointer 301. Thus, the quantitation of its position in the field need not be done by discrete index points on the instrument.

The major advantage of the probe structures illustrated in FIGS. 1, 2 and 3 is that they are mechanically decoupled from the observing cameras and thus there are no encumbrances of mechanical linkages such as a robotic arm as has been proposed in the past. It is also true that these probes can be made relatively simply and to be disposable so that the surgeon can throw the probe away after the procedure without incurring great expense.

Figure 4:
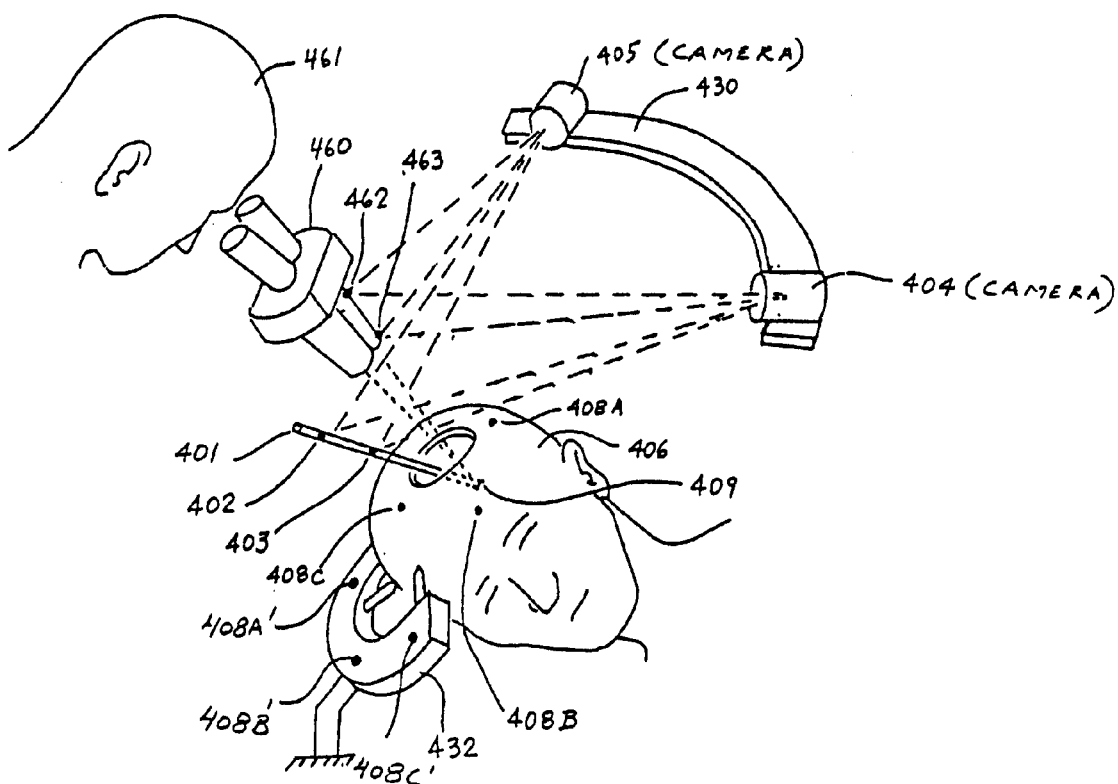
FIG. 4 shows an embodiment of the present invention in which two cameras are used and they visualize the anatomical field together with a space pointer, index marks on the patient's anatomy and a microscope so as to relate the position and aim of the microscope to the anatomy and the space pointer.

FIG. 4 shows another embodiment of the present invention for use with optical digitizing viewing means which involves not only a probe 401, but also an operating microscope 460. The objective here is to determine quantitatively the relationship between the patient's head 406 and its anatomy within it, the space probe 401 and the operating microscope 460. The principle is essentially the same. The patient's head 406 is stabilized by the headholder 432. The microscope has index means 462 and 463 which may be LED point light sources as explained above. Similarly, the probe 401 has its index points 402 and 403. Cameras 404 and 405 are affixed to base platform 430 and view the entire field, microscope plus probe plus patient's head. Optical index points 408A, 408B, and 408C may be attached to the patient's scalp or to the headholder (points 408A', 408B' and 408C') to provide referencing to the anatomy of both the probe and the microscope. By this sort of viewing, the relationship of the position of the microscope 460 and its orientation relative to the anatomy can be determined as explained above. Thus, one can display on a graphics means the field of view in which the microscope is viewing relative to the anatomy. In that regard, see the above referenced textbook, Computer Graphics: Principles and Practice. Accordingly, when computer graphics representations of the anatomy have been made, then computer graphics of the field view with a microscope can also be represented on the graphics display means and, thus, the relationship between what the surgeon 461 is seeing and the computer reconstructed field may be made. This is very important in planning as well as interactive surgical resections. At the same time, the probe 401 may be inserted into the field and the position of its tip 409 can be represented within the actual microscopic viewing field of the microscope 460. The entire surgical array of instruments may be represented graphically so that interactive correction and management of the operation can be made by the computer systems. One can also put other instruments within the field such as scalpels, probes and other devices which the surgeon commonly uses, these being indexed by fiducial marks or simply visualized directly by the cameras and representations of them put onto the graphics display means.

Thus by the index points that we have alluded to in FIGS. 1 through 4 and the associated embodiments, one can relate the various structures including anatomy, probes, microscopes and other instruments together in one graphics display. It should also be said that once this relationship has been established, then the cameras which see the actual objects themselves can make direct overlays of the objects as seen with the graphic representation of these objects as calculated from the imaging prior to surgery. Thus, direct correspondence of shapes and objects can be instantly ascertained by the operator by merely overlaying the graphics display and the actual display together on the same graphics screen.

There are many variations of the embodiments shown in FIGS. 1 through 4. One does not need to have, for example, two video cameras or two or more video cameras pointing in the same plane. They could be non-coplanar and there could be an array of them to encompass a much larger field of space. Such a multi-camera display could be precalibrated or not precalibrated. The cameras could be monitored and stabilized by fixed fiducial points somewhere in the field so that the entire registration and synchronization of all cameras would be possible. The mounting on which the cameras are held could be movable and changed interoperatively to optimize the position of the cameras while maintaining registration with the subject field. The orientation of the cameras relative to the anatomy, microscope or probe could also be done without the need for fiducial lights such as sources 2 and 3 in FIG. 1 or index fiducial points 8A, 8B, and 8C in FIG. 1. Overall correspondence of the shape of the subject as viewed by the camera could be overlaid and optimized in its matching to the graphics representation of the anatomy taken from the images. Graphic rotation of the image data could be done so as to register the direction of view of the camera relative to the anatomy. This correspondence would then be done by shapes of subjects in the real field vs. shapes of subjects in the graphics field. Such optimization of the two shapes could be done and the direction of the camera thereby determined relative to the field of view. Once that is done, the orientation of the probe 1 or any other shaped object related to a probe could similarly be registered from the camera's point of view. Pattern recognition algorithms be used to determine the orientation of the probe 1 therefore relative to the orientation of the other subjects such as the head and its orientation relative to the cameras.

The present invention also recognizes the use of one optical camera. Although the examples above illustrate use of two or more cameras, there is utility in even using just one camera to view the surgical field. It can give you a two-dimensional representation in a projected view of the field. One can use this representation and the graphic representation from the image data to register the two views and, thus, align the graphic display in a "camera view." Thus pointers in the field of the camera can be registered directly on to the graphic display view. For example, a pointer moving on the surface of the skin would be registered relative to the graphic view so that you would know where that point is moving relative to this quantitative data that represents the skin and other anatomical structures below the skin. This would have more limited usefulness, but it could also be important. Thus, the application of mounting a single video camera to view a surgical field and representing that visual field on a graphic field so as to bring the two fields into alignment by manipulation of the graphic field in the computer has utility in the surgical setting.

FIG. 5 illustrates more specifically the use of one optical viewing camera and registration of its field by computer graphics to image data. In FIG. 5, a camera 505 which has been anchored via arm 550 near the surgical field, views the patient's head 506 and other objects nearby. The camera 505 is connected via cable 551 to a computer graphics display unit incorporating a screen 552. The computer graphics screen 552 is cooperatively connected to computer calculation means and storage means represented by a box 554 to produce an image as represented on the screen. The data in the storage means (in box 554) may be provided from a scanning source, e.g., a CT or MRI scanner or it may be a magnetic tape with corresponding data on it. The camera 505 is viewing the head and a representation of the head shows on the screen 552 together with image data indicated by the contours 553. In the field, it is probe 501 which is seen as representation 555 on the screen. Also, there is a surgical opening 507 and for completeness, the index marks 508A, 508B, and 508C which may aid in orienting what is seen by camera 505 to the graphics image data seen on screen 552. The headholder 532 and associated pins 533 hold firmly the head 506 relative to the camera 505. As shown on the screen 552, the corresponding index points 558A, 558B, and 558C are shown on the screen as well as the actual image of the anatomy and the space probe represented by image 553. Thus, if computer graphics representations of the same anatomy are simultaneously put on the screen, for example, in a different color, then those image data can be scaled, translated, and rotated such that they register with what is seen by the field of view of camera 505. By so doing, one has in perspective view a registration of the camera data with the image data. Thus when one looks at the probe representation 555, on the computer graphic screen 552 of the actual probe 501, one can see immediately the correspondence of that probe relative to the quantitative stereotactic image data anatomy. Thus in perspective view, one is relating the position of the probe to that stereotactic image data anatomy, and this can be a very useful adjunct to surgery. For example, if one wished to know where to make the surgical opening 507, one could move the probe 501 in actual space relative to the anatomy until one sees the probe in perspective view with its tip over the desired point relative to the image data anatomy seen on screen 552. That would instantly tell you that this is the place to make the surgical bone opening, for example. There are many other illustrations of the use and power of this one-camera approach.

Figure 6:
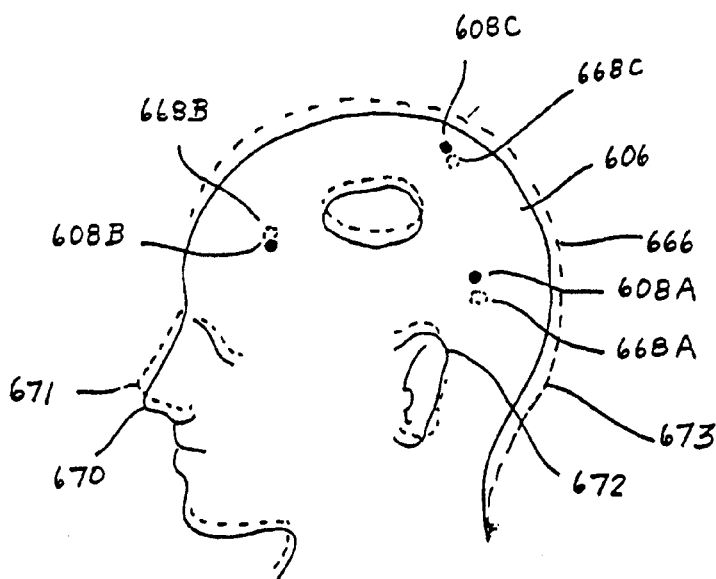
FIG. 6 shows a schematic representation of how camera field data would be registered in position and orientation to analogous image scan data on the same computer graphic display.

FIG. 6 shows how one might register camera anatomical data to image machine-acquired anatomical data as described in the paragraph related to FIG. 5. For example, in FIG. 6 the outline 606 represents the actual contour of the patient's head as seen by the camera 505 in FIG. 5. Also, the points 608A and 608B and 608C are shown as dots and these too are seen by the camera. Furthermore, anatomical landmarks such as 672, the tip of the ear, and 670, the tip of the nose, may be seen by the camera 505 in FIG. 5. The dashed-line contour in FIG. 6 shows a similar contour reconstructed in a perspective view from, for example, CT slice image data. Such image data can be stacked, can be surface rendered, and can be viewed and oriented from any different direction by computer graphics manipulation. Thus, it is possible to take such "dashed" image data representations, scale them proportionately, rotate them in space, and translate them, such that when you view the dashed and undashed contours on the computer graphics console, the operator can easily trim in the image data or the dashed line 666 such that it matches exactly the solid line 606 on the computer graphics screen. Such treatments of computer graphics data are disclosed in a textbook: Principles of Interactive Computer Graphics, McGraw-Hill Book Company, Newman and Sproul, 1979, incorporated by reference herein. For example, moving parts of an image is specifically treated in a section 17.3 at page 254. Also, in a similar way, one can make computer graphic manipulations to register the correspondence of the image points from the camera 608A, 608B, and 608C with the corresponding index points 668A, 668B, and 668C, which are illustrated by dashed points in FIG. 6. Registering these two sets of the same physical points in the computer graphics would be an attractable way of registering the entire two perspective views. Similarly, anatomical landmarks which are identifiable such as the computer graphic representation of the tip of the ear 673 and the tip of the nose 671 can be represented and corresponded to the analogous points 672 and 670 from the camera data. The use of different colors, color washes, color transparencies, and other powerful graphic standards as well as mathematical algorithms to optimize the correspondence of these two perspective views are easily put into play at this point to do the job.

Figure 7:
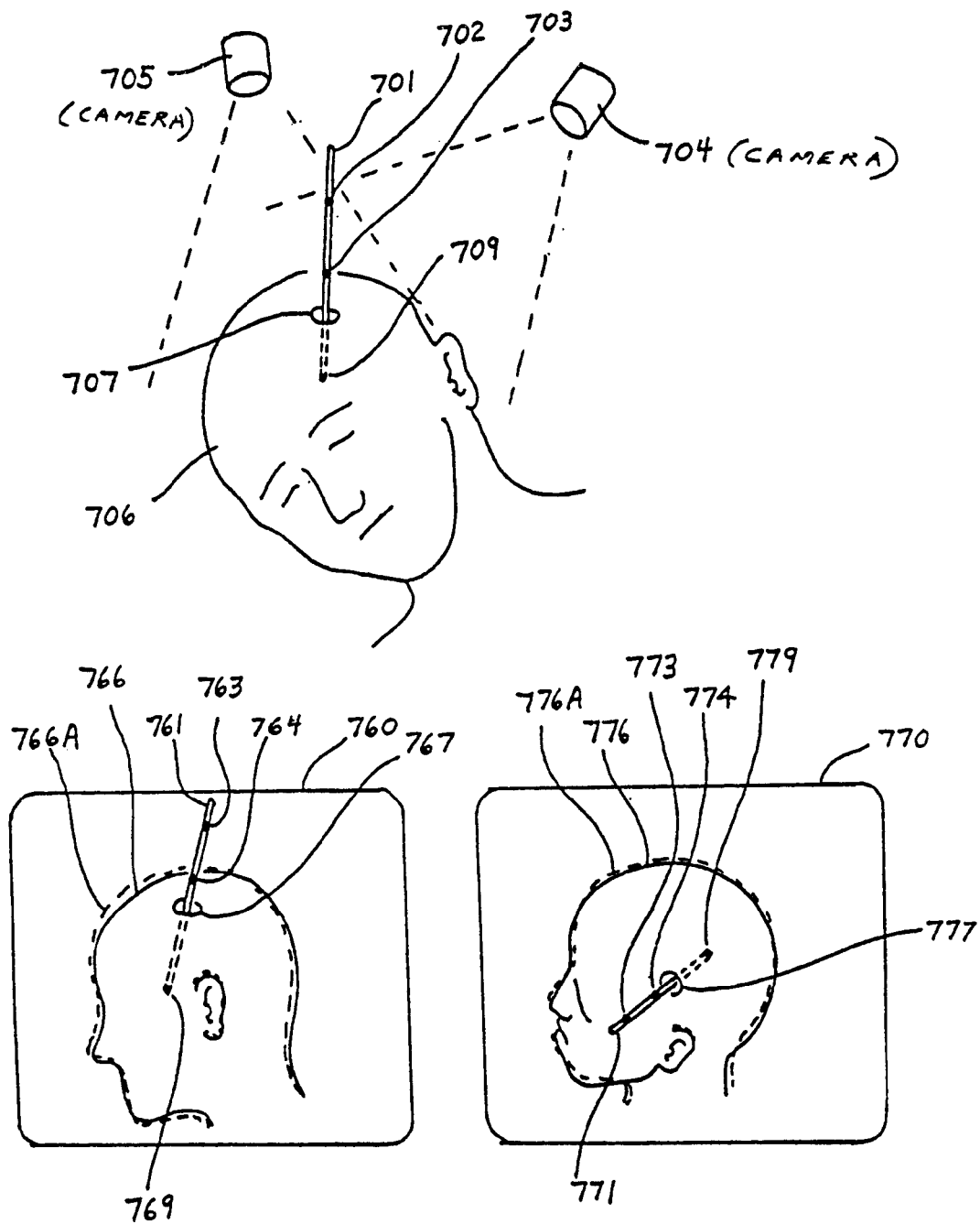
FIG. 7 shows a schematic view of two cameras looking at the anatomical subject with corresponding graphic views both of the camera, readout and field of view and of the computer graphic representation of the same view.

FIG. 7 illustrates another embodiment of how more than one camera can be used for computer graphic registration and corresponding quantification of an optical view. In the upper portion, one sees two cameras 704 and 705, pointing at arbitrary non-identical directions towards the subject 706. The fields of view are shown with the dashed lines. There is a cranial hole 707 with a probe 701 in it to the depth of the brain with the tip 709 inside the head. Index points 702 and 703 on the probe may or may not be present and are analogous to those discussed in FIG. 1. Each of the cameras will have views as illustrated in the lower portion of FIG. 7 and are displayed on the computer graphic display means 760 and 770. The display means 760 represents, for example, the view of camera 704 and one sees the solid line 766 which is the optical outline as seen by camera 704 of the patient's head. Similarly, the probe 761 is seen through the burr hole 767. By computer graphic translation, rotation and scaling, one can adjust the computer graphic view so that it matches the anatomical view, i.e. the computer graphic perimeter 766A indicated as dash line exactly matches 766. In this way, one knows that one has reproduced graphically with the dashed curve the projected view as seen by 704. Analogously, camera 705 will have its view as seen in graphic display 770 of the outline of the head 776 being matched to the graphic outline of the head 776A. Obviously, index marks, grids or lines on the patient's scalp might help in this registration of the two camera views. Once these views, however, have been registered, uniquely identifiable points in both views can give information on the exact 3-dimensional coordinates of those identifiable points relative to the anatomy as seen from the image data. For example, the points 763 and 773 are identical and correspond to the physical point 702 on the probe. On each of the views 760 and 770 this point represents a projected line as seen from the respective camera. The two lines from the two cameras intersect at a unique point and this can easily be determined as a unique 3-dimensional point referenced to the data from the image scanner as stored in the computer. Thus, the two points 702 and 703 can be determined quantitatively in space relative to the anatomical data, and thus, the quantitative position of the probe and any point on the probe can be determined relative to the image data. In particular, the end of the probe represented by point 709 which is in the depth of the brain and indicated on the graphics display as 769 and 779 respectively can be determined, i.e. the 3-dimensional coordinates of that point relative to the 3-dimensional image anatomy can be determined. Thus, there is no particular need for special index marks as shown in FIG. 1. Mere registration of existing anatomical structures relative to camera view and the image data would be sufficient for a full 3-dimensional representation of any instrument such as the probe in FIG. 7 relative to the anatomy. Using special angles such as 90° or stereoscopic views of the cameras could be convenient for such 3-dimensional registration without prior calibration.

It also should be said that for fixed camera positions, the subject itself might be moved so that his optical representation matches the graphic representation. In most cases, it would seem simpler to do the movement of the subject's image data via software, than moving the anatomical subject relative to the cameras, however, both methods could be used for registration of the respective images.

The use of such camera registration with image data eliminates any need of camera field calibration or the need to know relative camera angles.

It should be stated that this technique and the rest of the discussion above is differentiated from a previous attempt at registration of computer graphics to anatomical viewing. This was done by Patrick Kelly in the 1980's, and is reported in the literature in several places. Kelly's approach was to move a surgical microscope to a direction that was determined by image scan data. He would then take reconstructed structures from the image data and project it on a "heads up" display so that the surgeon looking on the microscope could see a graphic representation of what he should be viewing in the microscope field. The procedure of Kelly's was to first calculate the position from graphics of his microscope in terms of the approach angles of the microscope to the anatomy. Once specifying these approach angles, he could superpose the simulated graphics next to the microscope view. There are important conceptual differences between Kelly's method and the method discussed here in the present invention. First, Kelly does not use information, qualitative or quantitative, in the camera view or microscope view to make the correspondence, registration, or quantification of what is seen in the camera view relative to the graphics data. Secondly, he never uses two cameras to quantify the field of the cameras and relate them to the graphic display. Thirdly, he does not use object-related or fiducial identification points seen in one or more camera views to register the views directly to the image data. Thus, Kelly's approach differs in a fundamental way from what is being claimed in this invention.

The present invention includes in its scope the use of one or more cameras in the context illustrated by FIGS. 1 through 7. It includes the use of a camera together with a computer and computer graphic means to register and relate optical viewing to image data from other scanning and imaging devices. It also relates to the use of such optical and image data correspondences to register and quantify the position of surgical tools such as the space probe or the microscope illustrated in the above examples. It is related to making the associated mathematical transformation from a coordinate system or perspective view seen by one or more cameras to a stereotactic coordinate system related to image data or a corresponding reconstructive perspective view of image data and associated coordinate information from such image data. It relates to the correspondence between objects both anatomical or surgical in a camera view to objects either anatomical or of an index or marker nature as represented from scanner data or extrapolated from scanner data in a computer or computer graphic system. This was given as a specific example from FIG. 1 in the relationship of a mechanical space pointer to index marks and these, in turn, to corresponding quantitative positions in space where index marks are known from image data. Registration of the camera viewing data to the image data may or may not involve index marks, index lines or index localizer devices. It may be done as illustrated in FIGS. 6 and 7 by visual or computer theoretic optimization of registration of camera and image data or camera and reconstructed image data or enhanced camera or manipulated image data. The invention further generalizes the concept of "a camera" to other camera-like devices. These might include an x-ray camera or an x-ray source which is point-like and projects through the anatomy to give the image on a detection plane at the opposite side of the anatomy. This data could be projectively reconstructed as though it were reflected light from a single camera as illustrated in the examples above. Thus, the invention subsumes the field of generalized camera viewing or projected image acquisition relative to CT, MRI or angiography acquisition from other imaging means and the registration thereafter to make correspondence between these two image acquisition modalities.

Using more than one camera enables the determination of three-dimensional coordinates and depth of perception. The examples on FIGS. 1 through 4 illustrate this by use of a probe with two fiducial points on it that can be seen and digitized by the two camera views. This invention relates to the use of a video camera to quantitatively relate to graphic display data taken from other imaging means. The correspondence of the data are illustrated by the embodiments above and the discussion above, but those skilled in the art could think of other implementations of the same invention concept. For example, the use of two fiducial points on the probe can be extended to other types of optical fiducial means such as lines, other arrays of points, other geometric patterns and figures that can be recognized easily by computer graphics, artificial intelligence, etc. The two points illustrated in the figures could be replaced by a line of light and one or more discrete points to encode the direction of the object. The object itself could be recognized by the computer graphics as a line merely by having it of a reflective material or a particular color. The space pointer, for instance, could be white or green and thus show up differently on the TV cameras and in the video display so as to recognize it as the pointer.

What is claimed is:

1. A surgical system, which comprises:
   computer memory for storing and providing image data of a patient's anatomy referenced in three-dimensional image data coordinates;
   a surgical device;
   an optical index element mountable in known relation to the surgical device;
   an optical sensor mechanism arranged to provide a field of view encompassing the patient's anatomy and the surgical device and to detect the optical index element thereby providing location data, referenced in the image data coordinates, of the surgical device with respect to the image data of the patient's anatomy; and
   a computer display for displaying a composite image representative of the image data and position of the surgical device in relation to the image data of the patient's anatomy.

2. The system according to claim 1 wherein the optical sensor mechanism includes at least two optical sensors to provide at least two fields of view encompassing the patient's anatomy.

3. The system according to claim 1 wherein the optical sensor mechanism includes a camera apparatus having an optical sensor array.

4. The system according to claim 1, including a body index element attachable to the patient's anatomy, the body index element being at a known position relative to the patient's anatomy and referenced in the image data coordinates.

5. The system according to claim 1, including a mechanical holder adapted for mounting to the patient's anatomy, the mechanical holder including a holder index element detectable by the optical sensor.

6. The system according to claim 1 wherein the surgical device is a microscope.

7. The system according to claim 1 wherein the surgical device is a surgical probe.

8. A surgical system, which comprises:
   a surgical device;
   computer memory means for storing and providing image data of the patient's anatomy in scanner data coordinates;
   optical index structure including a plurality of optical index elements arranged in known relation to the surgical device;
   a camera apparatus having at least two fields of view encompassing the patient's anatomy and the optical index elements to provide current position data thereof;
   correlation software for correlating the current position data into the scanner data coordinates; and
   a display for displaying a composite image representative of the image data and current position data.

9. A surgical system, which comprises:
   a surgical device;
   memory means for storing and providing image scanned data representative of the patient's anatomy in three dimensions;
   camera means including at least one camera, the one camera having a field of view containing the patient's anatomy and the surgical device, thereby to provide camera image data of the patient's anatomy and current location of the surgical device;
   a computer graphic processing means for translating, scaling and thereby matching the camera image data of the patient's anatomy with respect to the image scanned data provided by the memory means to provide composite graphic image data of the patient's anatomy and the surgical device; and
   a computer display for displaying a composite graphic image based on the composite graphic image data of the patient's anatomy and the surgical device.

10. The system according to claim 9 wherein the computer display includes at least one video monitor for providing the composite graphic image.

11. The system according to claim 9 further including a body index element adapted for attachment to the patient's anatomy.

12. The system according to claim 9 further including an equipment index element attached in a known position relative to the surgical device.

13. The system according to claim 12 wherein the equipment index element includes optically detectable objects.

14. The system according to claim 9 further including a mechanical holder adapted for mounting to the patient's anatomy, the mechanical holder including optically detectable objects.

15. A process for providing a simultaneous graphic display showing the position of a surgical device with respect to a patient's anatomy, which comprises the steps of:
   storing scanned image data taken of the patient's anatomy in three dimensions;
   optically sensing a plurality of fields of view with at least two cameras, each field of view encompassing the patient's anatomy and the surgical device, whereby to produce camera image data of the patient's anatomy and the surgical device;
   graphic processing the scanned image data and the camera image data thereby to produce a combined and matching graphic image indicative of the patient's anatomy and the surgical device in three dimensions; and displaying the combined graphic image simultaneously representative of the patient's anatomy and the surgical device.

16. The process according to claim 15 wherein the step of processing includes the steps of translating, scaling, rotating and/or matching the camera image data with respect to the scanned image data.

17. The process according to claim 15 further including the step of scanning the patient's anatomy with a scanning device to obtain the scanned image data of the patient's anatomy.

18. The process according to claim 17 further including the step of attaching a body index element in a known position to the patient's anatomy prior to the steps of scanning and optically sensing.

19. The process according to claim 18 further including the step of computing spatial coordinates of identifiable points of the patient's anatomy using positional data of the body index element to provide the combined graphic image of the patient's anatomy, the step being performed in association with the step of graphic processing.

20. The process according to claim 17 further including the step of attaching an equipment index element in a known position to the surgical device prior to the steps of scanning and optically sensing.

21. The process according to claim 17 further including the step of mounting a mechanical holder to the patient's anatomy, the mechanical holder having a holder index element attached in a known position thereto.

22. The process according to claim 15 further including the step of calibrating the at least two cameras using uniquely identifiable points in the patient's anatomy.

23. The process according to claim 22 wherein the step of calibrating is performed using naturally identifiable points in the patient's anatomy.

24. The process according to claim 22 further including the step of attaching a body index element in a known position to the patient's anatomy, wherein the step of calibrating is performed using positional data of the body index element.

* * * * *